(12) United States Patent
Julius et al.

(10) Patent No.: US 8,457,361 B2
(45) Date of Patent: Jun. 4, 2013

(54) OPTICAL SEMI-QUANTITATIVE 100% FILLING CHECK OF PHARMACEUTICAL CAPSULES ON CAPSULE-FILLING MACHINES

(75) Inventors: Klaus Julius, Marienheide (DE); Peter Stoeckel, Appenheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1163 days.

(21) Appl. No.: 12/090,643

(22) PCT Filed: Oct. 18, 2006

(86) PCT No.: PCT/EP2006/067557
§ 371 (c)(1),
(2), (4) Date: Sep. 3, 2008

(87) PCT Pub. No.: WO2007/045670
PCT Pub. Date: Apr. 26, 2007

(65) Prior Publication Data
US 2009/0146087 A1    Jun. 11, 2009

(30) Foreign Application Priority Data
Oct. 19, 2005 (DE) .......................... 10 2005 049 958

(51) Int. Cl.
*G06K 9/00* (2006.01)
(52) U.S. Cl.
USPC ........... 382/110; 382/203; 382/266; 356/627; 356/626; 356/634; 356/239.6; 209/525; 209/529; 209/598; 209/659
(58) Field of Classification Search
USPC ..... 356/2, 485, 489, 495, 511, 514, 601–613, 356/626, 394, 426, 427, 239.1–239.7, 240.1, 356/237.2, 243.4
See application file for complete search history.

(56) References Cited

U.S. PATENT DOCUMENTS

| | | | | |
|---|---|---|---|---|
| 4,143,770 A * | 3/1979 | Grimmell et al. | ............. | 209/558 |
| 4,144,970 A * | 3/1979 | McKnight et al. | ............. | 209/542 |
| 4,593,190 A * | 6/1986 | Kawasaki et al. | ......... | 250/223 R |
| 5,463,465 A * | 10/1995 | Yamamoto et al. | ........... | 356/394 |
| 5,523,560 A * | 6/1996 | Manique et al. | .......... | 250/223 B |
| 5,819,953 A * | 10/1998 | Julius et al. | ................... | 209/561 |
| 6,108,030 A * | 8/2000 | Yamamoto et al. | ............. | 348/91 |
| 6,345,487 B1 * | 2/2002 | Luciano et al. | ................... | 53/54 |
| 7,012,242 B2 * | 3/2006 | Tarozzi et al. | ............. | 250/222.1 |

OTHER PUBLICATIONS

John C. Russ, The Image Processing Handbook, CRC Press 2002.*

* cited by examiner

*Primary Examiner* — Chan S Park
*Assistant Examiner* — Mark Roz
(74) *Attorney, Agent, or Firm* — Michael P. Morris; Wendy A. Petka

(57) ABSTRACT

The invention relates to a method for monitoring the filling of a capsule with a medicament, a corresponding filing method and the corresponding devices. According to the monitoring method, after at least part of the capsule is filled with a given filling mass of given closed shape of medicament, in a first step, at least the filling mass located in the part of the capsule after filling is recorded with a digital image, in a second step, the shape of the filling mass located in the part of the capsule is determined from the digital image and, in a third step, the shape analysed to give an analysis of the filling in comparison with given shapes.

20 Claims, 7 Drawing Sheets

OPTICAL SEMI-QUANTITATIVE 100% FILLING CHECK OF PHARMACEUTICAL CAPSULES ON CAPSULE-FILLING MACHINES

RELATED APPLICATIONS

This application claims priority to International Application No. PCT/EP2006/067557, filed Oct. 18, 2006, which claims priority to German Patent Application No. 10 2005 049 958.9, filed Oct. 19, 2005, the contents of which are incorporated herein by reference in their entirety.

FIELD OF THE INVENTION

The present invention relates to a method of monitoring the filling of a capsule with a medicament, a corresponding filling method and the associated apparatus. In the pharmaceutical industry, powdered oral and inhaled preparations are packed into capsules, e.g. hard gelatine capsules. Various methods and machinery are known for filling the capsules. These resemble one another in that they all operate volumetrically. A predetermined metering volume is filled as homogeneously as possible with the medicament which is generally in powder form. A loosely cohesive powder cylinder is formed. This cylinder is then pressed out of the metering chamber and drops into the lower part of the capsule. After being filled the lower part of the capsule is sealed by fitting the cover onto it.

The known capsule filling machines operate at a high throughput, so that up to 250,000 capsules per hour are filled with powder. The measures used for quality control comprise a random sampling of the capsules to check for the correct fill quantity. The quality of the capsules is judged on the basis of the random samples and corresponding statistical calculation. Generally the samples are measured by weighing. This method is laborious, particularly for small fill quantities. This is because in this case the empty capsules additionally have to be weighed. Moreover there is no 100% checking of the capsules. Therefore with the random sampling there is an acceptance that for each batch of filled capsules found to conform to the specification, depending on the stringency of the statistical random sampling criteria, there will be a greater or lesser number of capsules that clearly do not meet the quality standards. This may constitute a health risk in individual cases when the medicament is taken and should therefore be avoided. There is therefore a fundamental need for a quality-control inspection of the capsules which on the one hand provides a 100% check of all the capsules and on the other hand can be carried out as far as possible without the inspection slowing down the filling process or the process of manufacturing the capsules.

For example, a method and apparatus are known from U.S. Pat. No. 3,969,227 in which two light beams are shone through the capsules. The filling in the capsules interrupts the light beams. Therefore, using the intensity distribution in the beam transmitted, conclusions can be drawn as to the level of filling of the capsules with powder. This method has disadvantages in that it only provides a purely qualitative statement as to whether the capsule has been filled or not.

Particularly with small fill quantities in the capsule the precision of the method is inadequate. The publication "Füllstandsmessung mit Ultraschall von pelletgefüllten Hartgelatinekapsels" [Measurement of fullness of pellet-filled hard gelatine capsules using ultrasound] by H. Krasowski, W. Pfiefer, G. Marquardt and U. Klass (Pharm. Ind. 57, No. 4, pages 328-332 [1995]) discloses a method of determining the level of filling of capsules in which the fill level of the capsule is determined purely by measuring the time taken for ultrasound to pass through. This process is only suitable for fillings which are homogeneously distributed in the lower part of the capsule. For capsules which are oversized by comparison with their filling the process cannot determine the level of filling with sufficient precision.

The publication "Automatische Füllkontrolle für die Abfüllung von Pellets in Hartgelatinekapseln" [Automatic filling monitoring for packing pellets into hard gelatine capsules] by W. Pfiefer, G. Marquardt and M. Rommel {Pharm. Ind. 49, No. 3, pages 291-297 {1987]) describes a method in which the surface of the filling of the lower part of a capsule is irradiated with a light beam and a spot of light is produced thereon. The level of filling of the capsule is determined by means of the size of the light spot that varies with the level of filling. This is the so-called Berghoff system. In another process discussed therein, the fill levels of a number of lower capsule parts are scanned using a scanning rod. If a rod is immersed too deeply this interrupts a light beam. This process is very inaccurate. Moreover, like the above mentioned process, it is suitable only for fillings that are homogeneously distributed in the lower part of the capsule. This latter process is suitable only for checking stationary capsules. The capsule has to be brought to a standstill after filling, which is technically laborious, and the manufacturing time is prolonged considerably.

The objective of the present invention is therefore to provide a method of monitoring the filling of a capsule with a powdered medicament and a method of this kind in conjunction with a filling operation, in which more effective and faster monitoring of the filling is achieved by comparison with the prior art. An apparatus which is advantageous for achieving this aim is recited in the independent claim. Some advantageous features are also the subject of the independent claims.

DESCRIPTION OF INVENTION

The method according to the invention is used to monitor the filling of a capsule with a medicament. It may be a hard gelatine capsule, for example. These capsules consist of a lower part and a cover, for example. After at least part of the capsule has been filled with a given fill mass of a given closed contour from the medicament, particularly a powdered medicament, according to the invention, in a recording step, at least the fill mass located in the capsule part after filling is recorded as an image, particularly a digital image, and in a subsequent evaluation step the filling is evaluated using the image recorded in the recording step.

In one embodiment, the capsule which is delivered for filling in a pre-closure position, for example, is separated into two parts by the application of a vacuum, before the monitoring process according to the invention. The lower capsule part, as an example of a part of a capsule which is to be filled, is filled with a given fill mass of a given closed contour.

The fill mass, in the case of a medicament already in powder form, is obtained from the metering volume and the density of the medicament. The medicament may be an orally administered or inhaled drug. The powder is lightly compacted in the metering chamber. The plug of powder generally survives the free fall from the metering device into the lower capsule part unharmed. The shape or sharp contour of the plug of powder is retained. In many cases, the metering volume and hence the fill mass formed therein are cylindrical.

In the recording step of the process according to the invention, at least the fill mass contained in the capsule part after filling is recorded as an image. For example, an electronic camera and suitable optical means are directed into the open capsule part and an image is taken. For example, the image is recorded directly by a camera equipped with a digital image converter or an electronic image of a camera is digitised using an additional converter. The image may be in the form of a grey scale image in one embodiment. For recording the image, according to one embodiment, means are provided for illuminating the inside of the capsule part. For example, the interior of the capsule is illuminated from above for the recording. Thus, a semi-reflecting mirror may be arranged above the capsule part to allow it to be simultaneously illuminated and recorded by means of this mirror. The fill mass can then be captured particularly easily, for example, if the provision of a depression in the capsule part means that the fill mass regularly collects largely in this depression after filling and is thus always located in the same place.

In the evaluation step, the state of the fill mass located in the capsule part is determined from the recording. For example, the number of fragments in the recorded image or the degree of fracturing of the fill mass is determined. An evaluation of the filling is carried out in order to ascertain, for the individual filling, whether filling has been satisfactory or not. For example, unsatisfactory filling may occur if, during the release of the fill mass from the metering volume into the capsule part, there has been an incomplete release of the fill mass from the metering volume. Moreover, during the transfer of the fill mass into the capsule part, parts of the fill mass may have broken away, leading to incomplete filling. Moreover, there may have been some residual powder in the metering volume, which may lead to overfilling. The monitoring process according to the invention allows rapid and yet more accurate qualitative assessment of a capsule filling compared with the prior art. The process according to the invention is particularly suitable for capsules in which the fill mass makes up only a small fraction of the volume of the capsule. This is seldom the case for oral preparations but is frequently the case with inhalants.

In an advantageous embodiment of the process according to the invention, in the evaluation step, the contour, i.e. the outline of the fill mass contained in the capsule part, which is apparent from the observation, is determined from the imaging recording. The contour is then analysed in order to carry out an evaluation of the filling compared with the predetermined closed contour of the form mass or of the metering volume. If the two contours differ substantially from one another and/or if the contour in the comparison is highly fractured, there has a change to the outer contour of the fill mass during filling and the filling has been unsatisfactory. Thus the deviation from the contour, based for example on its overall configuration and/or on its characteristic properties such as constancy, i.e. smoothness, enables conclusions to be drawn as to whether the capsule part and hence the capsule has been filled insufficiently or to excess, i.e. in the last analysis this allows a qualitative assessment of the filling and, optionally based on the degree of deviation, a quantitative assessment of the filling. According to one embodiment in which the fill mass assumes only a small number of reproducible positions in the capsule part and/or has a highly symmetrical form (e.g. a spherical shape), the comparison of the absolute configurations of the contour in itself is sufficient to carry out an evaluation of the filling from a qualitative and possibly quantitative point of view. The process according to the invention comprising contour-related evaluation of the fill mass provides a particularly fast and effective method of evaluating the filling of capsules, particularly in those cases where the fill mass makes up only a small proportion of the volume of the capsule.

According to an advantageous embodiment of the process according to the invention, the recording is carried out using visible light by detecting the fill mass using light from the visible frequency range, or by shining such light through the capsule part. As a result, the process can be carried out comparatively easily and cheaply. The construction elements needed to carry out the process are robust and can be integrated comparatively easily into existing filling apparatus for pharmaceutical capsules, in view of their small dimensions.

In an advantageous embodiment of the method of monitoring the filling of a capsule with a medicament, the imaging recording is carried out by means of a recording that penetrates the capsule part. For example, the capsule is illuminated from below with intensive light to record an image. The contour of the filling shown in the image is thus obtained. The light intensity and its spectral distribution are selected in accordance with the optical properties of the capsule material which is to be illuminated and the other lighting requirements. Depending on the performance of the imaging recording the entire capsule, i.e. the capsule already resealed with the capsule cover after being filled, can be examined by transmitted light. For example, this is done using ultrasound or high intensity light and/or with a highly transparent capsule material. The transmitting recording ensures that the contour of the fill mass can be determined comparatively easily thanks to the high contrast between the area shaded by the fill mass and the remaining area and there is no need for any additional contrast-increasing image-processing measures.

Moreover, the transmitting recording ensures that the technical apparatus required for the process is comparatively limited. Because capsules are generally small in size, they are not easily accessible in the machine. Simultaneous optical illumination of the interior and optical detection through the opening in the lower capsule part is comparatively complicated.

In another advantageous embodiment of the process according to the invention for monitoring the filling, in the recording step the interior of the capsule part is fully captured in the imaging recording. This ensures that any parts that have broken away from the fill mass or other parts which have got into the interior of the capsule part or capsule are detected during the inspection and in one embodiment this is taken into account during the evaluation of the filling from a qualitative and possibly quantitative point of view.

According to another advantageous embodiment, the filled part of the capsule is moved during the recording step. As a result, the process can advantageously be implemented during transportation of the capsule or capsule part, e.g. during filling, without it having to be stopped, thereby interrupting the transportation and negatively affecting productivity.

According to another advantageous embodiment, in the recording step, the view from above into the interior of the capsule part is stored. It has been found that with a recording device arranged underneath the capsule part this device, e.g. its associated optical equipment such as lenses and mirrors, can easily become dusty. This negatively affects the capture of the fill mass or may lead to inaccurate evaluations. In other words the direction of recording described above means that the apparatus is less prone to faults and can be used universally for different capsule materials.

Another advantageous embodiment proposes that the contour line recorded is examined for concave areas in the evaluation step. It has been found that an examination for concave areas in the contour line provides particularly reliable information as to how irregular the contour of the fill mass has become, which can be put down to fractures in the fill mass and hence defective filling, in the last analysis.

In the evaluation step of one embodiment of the process according to the invention, the contour line recorded is approximated by convex matching and the length of the contour line recorded is compared with the length of the approximated contour line. It has been found that reliable information as to the state of filling can be obtained by comparing the contour lengths. For example, the pixel length of the digitally obtained contour line recorded (number of pixels along the contour line) is determined and compared with the length of a curve which is obtained by convex enveloping of the curve obtained. The quotient of the enveloping curve, i.e. the approximated contour line by the actual contour line, yields a so-called convexity parameter alpha. The smaller this turns out to be, the more concave and irregular regions there are in the periphery of the fill mass, which can be put down to fractures in the fill mass and hence defective filling.

The threshold value for the convexity parameter is determined by the skilled man using as comprehensive a collection of test images as possible. These images come from capsules which have been weighed on tare and gross weight scales. Therefore, the mass of powder shown in the images is known precisely to the microgram. On the basis of these images the limit for the convexity parameter alpha is fixed so that the poorly filled capsules can be distinguished from the correctly filled ones with high definition.

In another advantageous embodiment the given contour is prescribed by means of a cylindrical fill mass. It has been found that the cylindrical shape is particularly suitable for carrying out an especially reliable evaluation of the filling from a qualitative and quantitative point of view, on account of its clear convex curvature ratios. Because of the clear convex curvatures of the surface of the fill mass, any irregular transitions or concave transitions caused by fractures in the contour line recorded are easily detected. As a result, the process is very reliable.

In the evaluation step of another advantageous embodiment, on the one hand the contrast is increased and on the other hand grey or coloured gradations in the image are reduced. Ultimately, this leads to easier recognition of the contour line in the image.

According to another advantageous embodiment, in the process according to the invention, the image is converted in the evaluation step into a binary image by a suitable choice of threshold value for the intensity. The threshold value is given, for example, by means of the lighting conditions and lighting sensitivity of the recording equipment and is set by the skilled man. By conversion into a purely binary image the amount of data can be reduced substantially and the digital image analysis in relation to the contour line which is to be determined can be dramatically speeded up.

In another embodiment of the process according to the invention, the image is subjected to morphological edge recognition in the evaluation step in order to detect the contour line.

Another embodiment provides that the image is inverted in the evaluation step in order to simplify the evaluation.

The invention further relates to a process for the continuous mechanical filling of capsules with a medicament, in which in each case at least part of the capsule is filled with a given fill mass of a given contour from the supply of medicament and moreover the filling is monitored according to one of the embodiments described above. During continuous mechanical filling this is carried out by the so-called inline method, i.e. the filling is carried out in the manner of a conveyor belt. The monitoring process in the embodiments described above allows total monitoring of the capsules, in synchronism with the filling process, thanks to the comparatively high speed at which the detection and analysis of the fill mass take place. For example, filling processes of this kind operate with a delivery rate of 80,000 capsules. As the monitoring process according to the invention takes a period of considerably less than 45 ms to monitor a single capsule, the monitoring process according to the invention can easily be combined with the known filling processes to achieve a total and effective quality control. The filling process may be, for example, a so-called packing process in which the metering volume is provided with matrix discs having corresponding bores. Depending on the results of the monitoring the respective capsule is rejected if necessary. For example, the capsule or the filled lower capsule part is ejected from the stream of other capsules by a jet of air during further transportation. In one embodiment the capsule deemed to be defectively filled is rejected after a delay of about 450 ms after filling. In the mean time, for example, the sealing of the lower capsule part is completed or it is transported on for packaging. This allows sufficient time for any possible delay in evaluation.

According to another advantageous embodiment of the process of continuous mechanical filling, the filling comprises knocking the fill mass into at least part of the capsule. It has been found that knocking the fill mass in the respective capsule part is a very suitable method of detecting any inhomogeneity of the fill mass which leads to unsatisfactory filling and which is associated with instability of the fill mass by the break-up of ingredients of the fill mass, and that in this way defective filling can be reliably detected. Knocking after free fall is sufficient.

In another advantageous embodiment the medicament is in powder form. It has been found that the combination of powdered medicament and the knocking in of the fill mass consisting of it is particularly suitable for reliably detecting inadequate filling. With a drop height of about 14 mm and an intended weight of fill mass of 5.5 mg, in the case of a powdered composition of fill mass and an inhomogeneous composition resulting from unsatisfactory filling, ingredients of the fill mass will reliably break up, and these can be easily and reliably detected by their pronounced effect of changing the contour of the fill mass and optionally by the presence of other fragments of the fill mass in the capsule.

In another advantageous embodiment filling is carried out using the pipette principle. The pipette principle is described below by reference to an example. Whereas in the packing process the metering volume is formed by matrix discs with corresponding bores, in the pipette the metering volume is produced by a defined withdrawal of a steel plunger in a steel sleeve. Then the pipette is immersed to a specified depth in a bed of powder consisting of the medicament, this powder being as homogeneous as possible. Powder is forced into the cylindrical metering volume which is open at the bottom until the powder totally fills the volume and thus forms a cylindrical fill mass. The pipette is then removed from the bed of powder. It passes through a suction pathway in which it is freed from any powder adhering externally. At the same time the open bottom of the pipette slides over a carefully aligned flat surface. In this way the excess powder is also removed from the bottom and the bottom of the powder cylinder in the metering volume is smoothed off. The pipette emerges from the suction pathway and a little later assumes a position directly above an open lower capsule part. The plunger of the pipette then forces the powder cylinder, which has a precisely defined volume, out of the metering chamber. An abrupt upward and downward movement of the plunger causes the powder cylinder to detach itself from the endface of the plunger. The distance of, for example, about 14 mm to the bottom of the lower capsule part is traveled by the cylindrical fill mass in free fall. It has been shown that the monitoring process according to the invention can advantageously be combined with the pipette process.

The invention further relates to a device for performing the processes described above which comprises at least means for digital image recording and means for digital image analysis. The means for digital data processing during image analysis and recording advantageously allow rapid and hence 100% monitoring of the filled capsules or capsule parts.

In an advantageous embodiment the means for digital image recording comprise at least one CCD (Charge Coupled Device) or CMOS image converter, to allow particularly rapid image capture and the use of a comparatively small and hence space saving camera.

In another advantageous embodiment, the means for image recording comprise at least one LED or a laser. In this way it is possible to achieve a very intense light for illuminating the capsule part or capsule. This has the advantage that in spite of the shuttering of the imaging optics which is necessary for a certain sharpness, it is possible to select such short exposure times that the signal to noise ratio in the CCD, for example, is sufficient. On the other hand, the intensity of illumination can be increased by the use of an LED or laser such that the filled capsule part is captured in an image during the transporting movement of for example up to 1.30 m/s. The motion blur is so slight with an exposure time of 50 μs that it is negligible for the evaluation purposes. The capsule therefore does not have to be laboriously mechanically slowed down or stopped during transportation in order to record an image. Moreover, an LED can briefly be subjected to current levels which are far above the permitted continuous current.

In another embodiment the means for digital analysis of the image comprise a computer.

Figure 1:
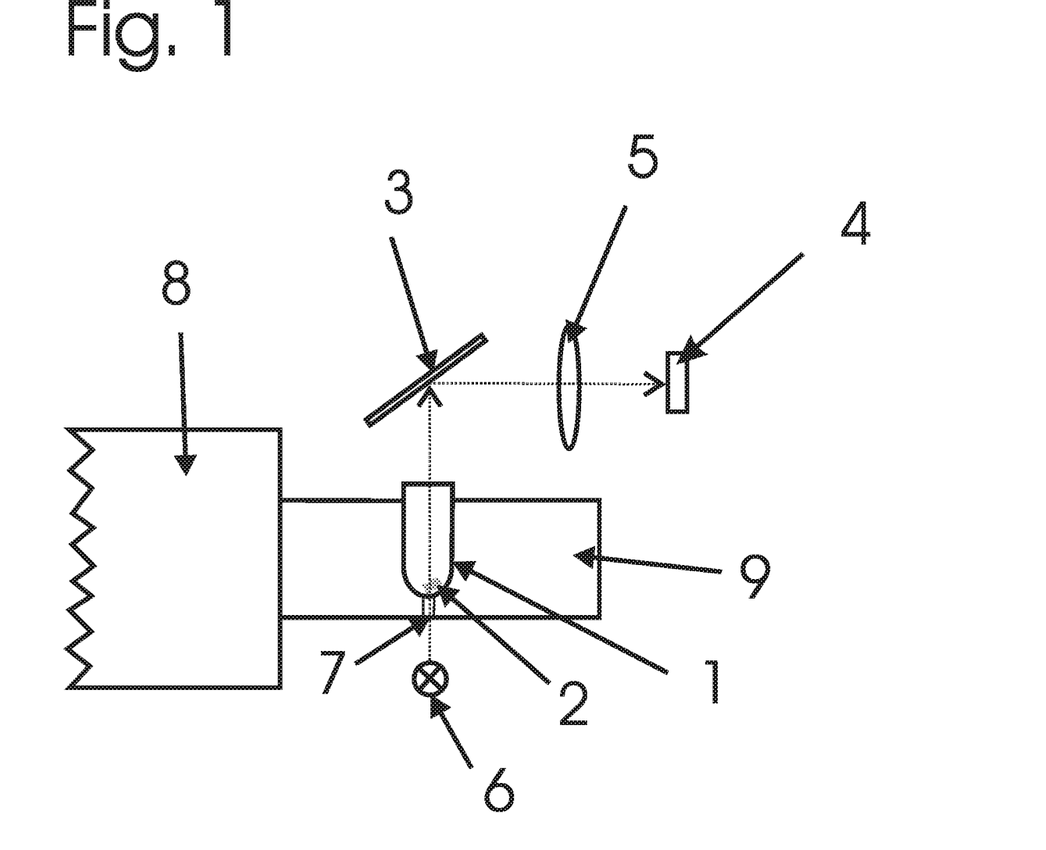
FIG. 1: Apparatus for filling and monitoring process

An embodiment of the monitoring process according to the invention which is used together with a filling process operating by the pipette principle is described below. A detail of the associated apparatus is schematically shown in FIG. 1.

The lower capsule parts 1 are each placed in stainless steel matrices which are in turn held by carriages 9 of a transporting system 8 of the filling installation. These carriages 9 travel along circular tracks, with cam control, in a horizontal plane underneath the pipettes (not shown). On this track, just behind the position where the lower capsule part 1 is filled with the fill mass consisting of powder, there is a region in which the carriages 9 with the matrix are largely exposed and easily accessible. Using a CCD camera 4 and associated optical means 3, 5, an image of the open lower capsule part 1 is recorded from above shortly after filling has taken place and the images are passed on for evaluation. For this purpose the camera images are transmitted to a computer and evaluated therein using a suitable algorithm. To assist with the evaluation of the images and, in particular, to make them as error-proof as possible, the images have increased contrast. In this respect it is not a good idea to illuminate the fill mass 2 in the lower capsule part 1 solely from above. Instead, it has proved advantageous to illuminate the lower capsule part 1 from below with an intense flash of light and to record the image with back light, as shown by the dotted arrows in FIG. 1. For this, there is a through-hole 7 in the carriage 9 and in the matrices in which the lower capsule parts 1 are held. The lower capsule part 1 is illuminated by means of a light-emitting diode 6 arranged underneath the plane of movement of the carriage 9.

Above the plane of movement of the carriage there is a mirror 3 which reflects the light transmitted through the lower capsule part 1 at right-angles and is projected through an objective 5 onto the CCD chip 4 of a camera. The carriages with the lower capsule parts travel at a track speed of about 1.30 m/s between the light source and mirror. As the capsules have a diameter of only about 5 mm, a correspondingly large imaging scale is used. To ensure that sufficiently sharp images are obtained even under these conditions, correspondingly short camera exposure times are used. To achieve a good signal to noise ratio in spite of the short integration time of the CCD chip 4 and to avoid having to open the shutter of the objective too widely in the interests of adequate sharpness, the capsule is illuminated with very intense light from an LED 6. It has been found that corresponding light intensities can be obtained easily and reliably using light emitting diodes (LEDs). The camera exposure time is 50 Us, for example. During this time the lower capsule part is moved on by about 65 μm. The blurring of the image caused by the motion is negligible.

The images recorded are transmitting to a computer and evaluated immediately. If the capsule filling machine is operated at a standard speed of 80,000 capsules per hour, 45 ms are available for the complete cycle of image capture and evaluation. If there is a delay in evaluating an individual image as a result of various factors connected with the operating system and the software for the image evaluation, the image or the incoming images is or are stored intermediately, for example using a ring buffer. This ensures that no images are lost and the clear allocation of the images to the filling devices is maintained. However, for each image the results of the evaluation will be obtained after not more than 450 ms because after this time the capsule in question will have arrived at the jet provided for the ejection process, which will blow the capsule into the reject container if necessary.

The evaluation algorithm functions as follows, according to one embodiment:
the algorithm recognises the position of the lower capsule part in the image recorded, which may be necessary for reasons of the mechanical variability of the machine and the consequent change in position of the lower capsule part. It masks any areas of the image that are outside the lower capsule part and recognises broken or otherwise damaged fill masses. If additional lumps of powder of a certain minimum size are present in addition to the fill mass, these are also detected.

Figure 2:
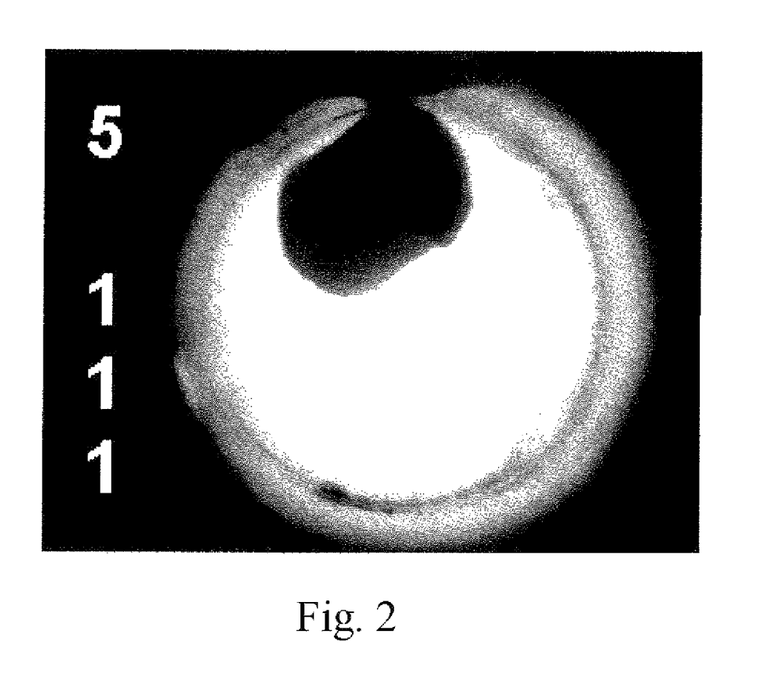
FIG. 2: Grey-scale image showing identifier and allocation of capsule part to image
Figure 3:
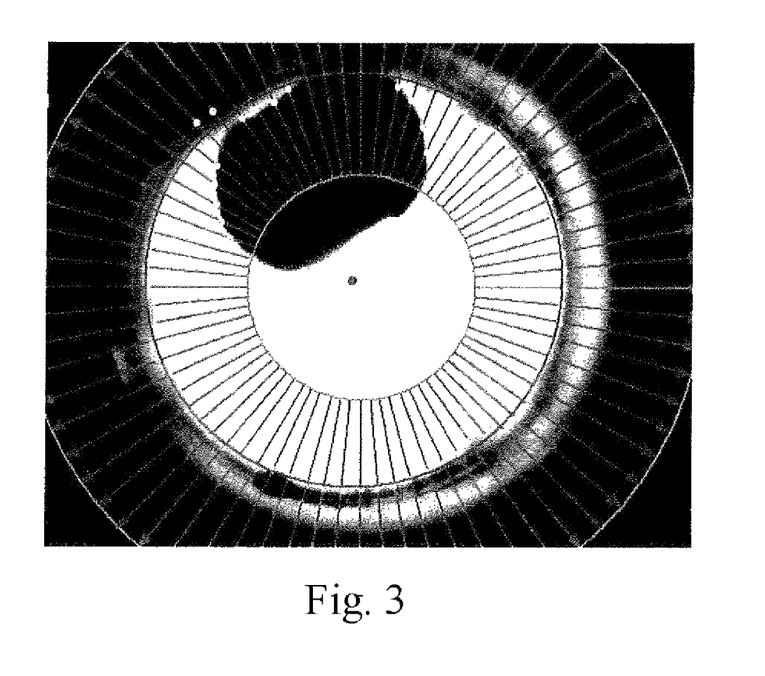
FIG. 3: Capsule located in the image
Figure 4:
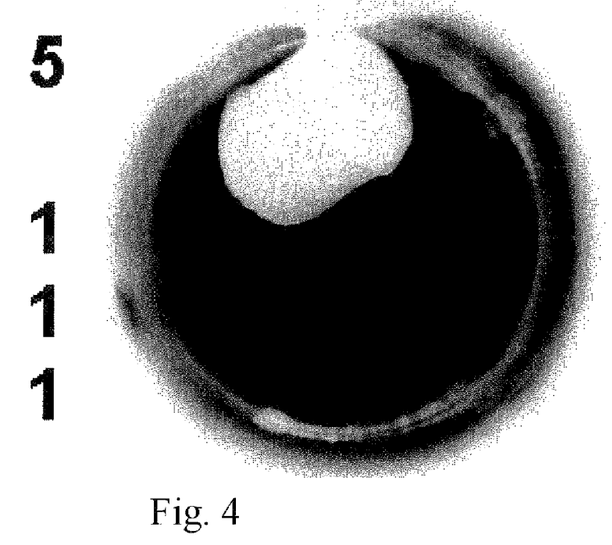
FIG. 4: Inversion of image
Figure 5:
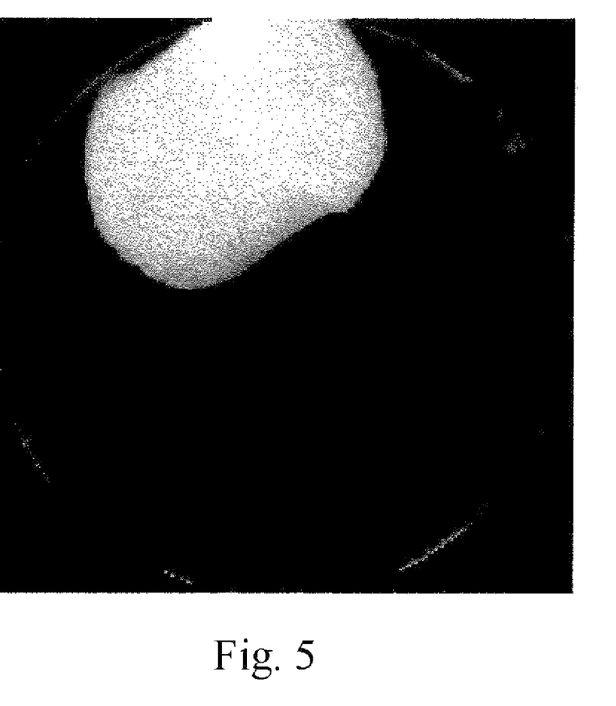
FIG. 5: Image being masked so that only region inside the capsule remains
Figure 6:
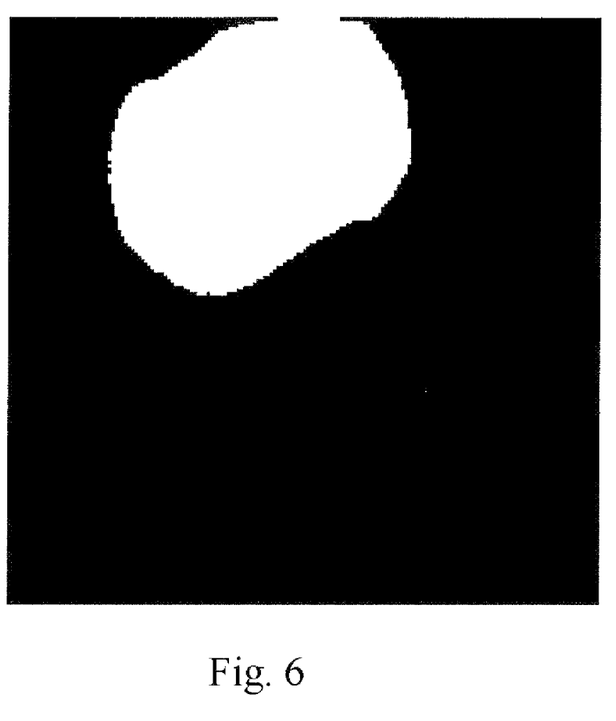
FIG. 6: Grey-scale image converted into binary image
Figure 7A:
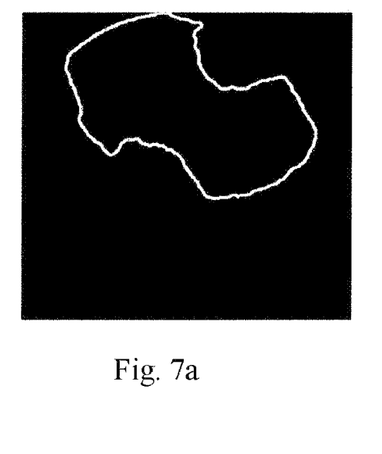
FIG. 7*a*: Original recorded contour of circumference of a broken fill mass
Figure 7B:
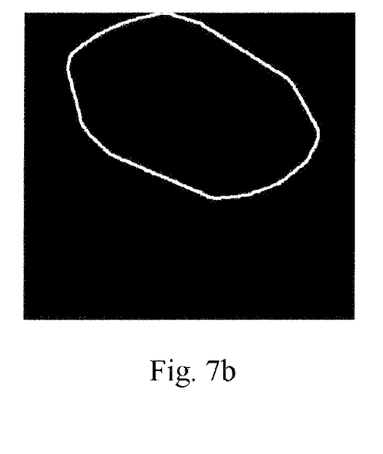
FIG. 7*b*: Shape of the recorded contour approximated by a convex envelope
Figure 8A:
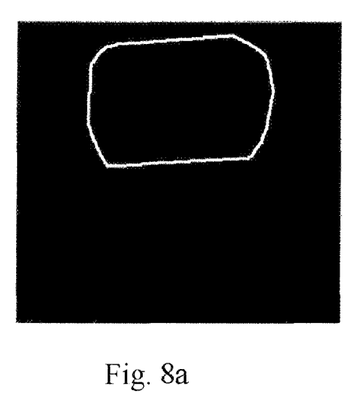
FIG. 8*a*: Original recorded contour of circumference of a broken fill mass
Figure 8B:
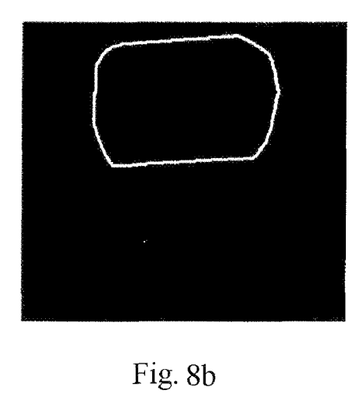
FIG. 8*b*: Shape of the recorded contour approximated by a convex envelope

Specifically, the image processing comprises the following steps:
1. A camera records a grey scale image, and an identifier is faded into the image in order to provide a clear allocation of capsule part to image, as shown in FIG. 2.
2. As the lower capsule parts may not always be seen in the same position, the capsule is located in the image, as shown in FIG. 3.
3. The image is inverted, as shown in FIG. 4.
4. Then the image is masked so that only the region inside the capsule still remains, as shown in FIG. 5.
5. The grey scale image is converted into a binary image using a suitably fixed threshold value, as shown in FIG. 6.
6. A broken fill mass is characterised in that the contour of the circumference has concave regions. The concave regions are detected by means of the convexity parameter. FIGS. 7a and 8a each show the original contour, i.e. the recorded contour. FIGS. 7b and 8b each show a shape of the recorded contour, approximated by a convex envelope. The convexity parameter alpha is equal to the quotient of the circumference of the convex approximation and the circumference of the original contour. In the case of FIGS. 7a and 7b, for example, an alpha value of 0.903 is obtained, whereas the alpha value of FIGS. 8a and 8b is 0.994. Accordingly, FIG. 7a or 7b corresponds to a defective filling of the lower capsule part, whereas FIGS. 8a and 8b correspond to satisfactory filling with an alpha value of roughly 1.

Figure 9A:
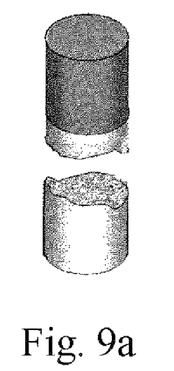
FIG. 9*a*: Illustration of fill mass consisting of powder that has not properly fallen off the plunger
Figure 9B:
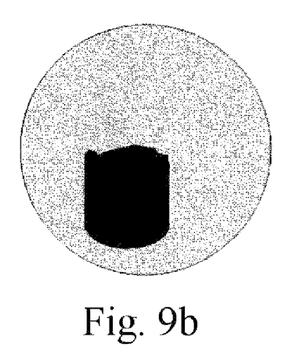
FIG. 9*b*: Illustration of fill mass in 9*a* during recording
Figure 10A:
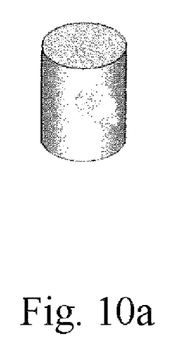
FIG. 10*a*: Illustration showing density of the fill mass being inhomogenous
Figure 10B:
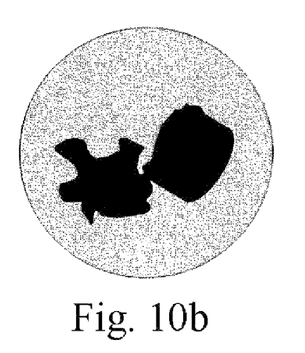
FIG. 10*b*: Illustration of fill mass in 10*a* during recording

FIGS. 9a, 9b, 10a and 10b illustrate the correlations between damaged fill mass, underfilled capsule and recorded contour. In FIG. 9a the fill mass consisting of powder has not properly fallen off the plunger. Some of the fill mass is still suspended. This may be due to the unfavourable adhesion characteristics of the powder, for example. During the recording, i.e. after filling and as shown in FIG. 9b, the fill mass per se has not broken up further but has fractured as a result of the partial breakaway from the plunger and is found to be defective by the monitoring process. In FIG. 10a the density of the fill mass is inhomogeneous, i.e. too low in parts, so that the density averaged over the entire volume is too low. This may be due, for example, to an inhomogeneous bed of powder or poorly filled insertion holes. As shown in FIG. 10b, the plug of powder has broken into several fragments after filling and during recording, as a result of insufficient stability, and defective filling can be detected particularly easily, among other things, by the presence of the fragments.

Figure 11A:
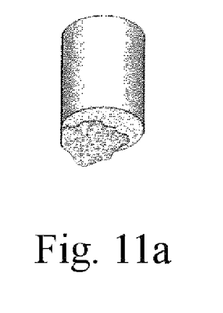
FIG. 11*a*: Illustration showing underside of the fill mass not cleanly imaged
Figure 11B:
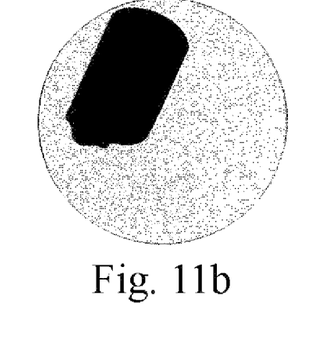
FIG. 11*b*: Illustration of fill mass in 11*a* during recording

FIGS. 11a, 11b, 12a and 12b illustrate the correlations between a damaged fill mass, an overfilled capsule and a recorded contour. In FIG. 11a the underside of the fill mass is not cleanly imaged. This may be due to a poorly arranged suction pathway, for example. During recording, i.e. after filling and as shown in FIG. 11b, the fill mass itself has not broken up, but because of the untidy shape at the bottom the shadow in the image is too large and too fractured. Therefore the monitoring process grades the capsule associated with the image as being a defective capsule.

Figure 12A:
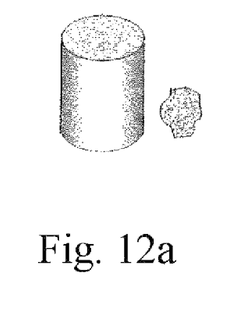
FIG. 12*a*: Illustration showing additional secondary particles
Figure 12B:
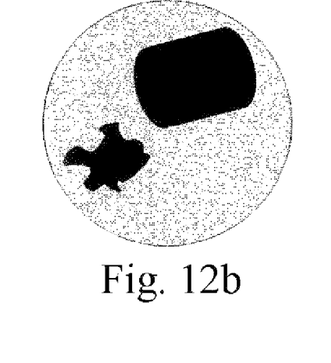
FIG. 12b: Illustration of fill mass in 12a during recording

FIG. 12a shows that besides the actual fill mass, additional secondary particles get into the lower capsule part. This may be due to powder adhering to parts of the metering device, soiled matrix discs and accumulations of powder above the tip of the plunger. During recording, i.e. after filling and as shown in FIG. 12b, the fill mass itself has not broken up. The secondary lumps are recognised by the image evaluation algorithm. If the area of these lumps is above a defined limit, the capsule probably contains too much powder and is deemed "defective".

The process according to the invention is used particularly preferably for capsules that contain powdered medicaments for inhalation, so-called inhalants. These powdered medicaments may contain an active substance in admixture with a physiologically acceptable excipient.

Examples of physiologically acceptable excipients include, for example, monosaccharides (e.g. glucose or arabinose), disaccharides (e.g. lactose, saccharose, maltose or trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose, glucose or trehalose is preferred, preferably lactose or glucose, particularly, but not exclusively, in the form of their hydrates. For the purposes of the invention, lactose is the particularly preferred excipient, while lactose monohydrate is most particularly preferred.

The excipients mentioned are usually characterised in that the excipient has an average particle size of 10-50 μm.

By average particle size is meant here the 50% value of the volume distribution measured with a laser diffractometer using the dry dispersion method.

The percentages given within the scope of the present invention are always percent by weight, unless specifically stated to the contrary.

In partic preferred inhalant powders the excipient is characterised by an average particle size of 12 to 35 μm, particularly preferably 13 to 30 μm.

Alternative pharmaceutical compositions are further characterised in that the excipient consists of a mixture of coarser excipient with an average particle size of 17 to 50 μm, particularly preferably from 20 to 30 μm and finer excipient with an average particle size of 2 to 8 μm, particularly preferably from 3 to 7 μm. Inhalant powders in which the proportion of finer excipient in the total quantity of excipient is from 3 to 15%, most preferably 5 to 10%, are particularly preferred.

When reference is made to a mixture within the scope of the present invention, this always means a mixture obtained by mixing together clearly defined components. Accordingly, when an excipient mixture of coarser and finer excipient fractions is mentioned, this can only denote mixtures obtained by mixing a coarser excipient component with a finer excipient component.

The coarser and finer excipient fractions may consist of chemically identical or chemically different substances, while inhalable powders in which the coarser excipient fraction and the finer excipient fraction consist of the same chemical compound are preferred.

For the application of the inhalant powders according to the invention using powder-filled capsules it is preferable to use capsules the shell of which is made from gelatine, cellulose derivatives, starch, starch derivatives, chitosan or synthetic plastics.

If gelatine is used as the capsule material, it may be used in admixture with other additives selected from among polyethyleneglycol (PEG), preferably PEG 3350, glycerol, sorbitol, propyleneglycol, PEO-PPO block copolymers and other polyalcohols and polyethers. Within the scope of the present invention it is particularly preferable to use gelatine in admixture with PEG, preferably PEG 3350. A gelatine capsule according to the invention preferably contains PEG in an amount of 1-10% (wt.-%), preferably 3-8%. Particularly preferred gelatine capsules contain PEG in an amount of 4-6%, a PEG content of about 5% being most preferred according to the invention.

If cellulose derivatives are used as the capsule material, it is preferable to use hydroxypropylmethylcellulose, hydroxypropylcellulose, methylcellulose, hydroxymethylcellulose and hydroxyethylcellulose. In this case, hydroxypropylmethylcellulose (HPMC), particularly preferably HPMC 2910 is used as the capsule material.

If synthetic plastics are used as the capsule material, these are preferably selected according to the invention from among polyethylene, polycarbonate, polyester, polypropylene and polyethylene terephthalate. Particularly preferred synthetic plastics for the capsules for inhalation according to the invention are polyethylene, polycarbonate or polyethylene terephthalate. If polyethylene is used as one of the particularly preferred capsule materials according to the invention, polyethylene with a density of between 900 and 1000 kg/m$^3$, preferably from 940-980 kg/m$^3$, particularly preferably 960-970 kg/m$^3$ is preferably used (high-density polyethylene).

The synthetic plastics according to the invention may be processed in various ways using production methods known in the art. The processing of plastics by injection moulding is preferred for the purposes of the invention. Injection moulding without the use of mould release agents is particularly preferred. This production method is well-defined and is characterised by being particularly reproducible.

These capsules may preferably contain about 1 to 20 mg, preferably about 3 to 15 mg, particularly preferably about 4 to 12 mg of inhalant powder. Preferred formulations according to the invention contain 4 to 6 mg of inhalant powder. Of equivalent importance are capsules for inhalation that contain the formulations according to the invention in an amount of from 8 to 12 mg.

The active substances that may be contained in the powdered medicaments are preferably selected from among the betamimetics, anticholinergics, corticosteroids, PDE4 inhibitors, LTD4 antagonists, EGFR-inhibitors, dopamine agonists, H1-antihistamines, PAF antagonists und PI3-kinase inhibitors.

The betamimetics used here are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]-sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one, 1-(4-ethoxy-carbonylamino-3-cyano-5-fluorophenyl)-2-(tert.-butylamino)ethanol, 2-hydroxy-5-(1-hydroxy-2-{2-[4-(2-hydroxy-2-phenyl-ethylamino)-phenyl]-ethylamino}-ethyl)-benzaldehyde, N-[2-hydroxy-5-(1-hydroxy-2-{2-[4-(2-hydroxy-2-phenyl-ethylamino)-phenyl]-ethylamino}-ethyl)-phenyl]-formamide, 8-hydroxy-5-(1-hydroxy-2-{2-[4-(6-methoxy-biphenyl-3-ylamino)-phenyl]-ethylamino}-ethyl)-1H-quinolin-2-one, 8-hydroxy-5-[1-hydroxy-2-(6-phenethylamino-hexylamino)-ethyl]-1H-quinolin-2-one, 5-[2-(2-{4-[4-(2-amino-2-methyl-propoxy)-phenylamino]-phenyl}-ethylamino)-1-hydroxy-ethyl]-8-hydroxy-1H-quinolin-2-one, [3-(4-{6-[2-hydroxy-2-(4-hydroxy-3-hydroxymethyl-phenyl)-ethylamino]-hexyloxy}-butyl)-5-methyl-phenyl]-harnstoff, 4-(2-{6-[2-(2,6-dichloro-benzyloxy)-ethoxy]-hexylamino}-1-hydroxy-ethyl)-2-hydroxymethyl-phenol, 3-(4-{6-[2-hydroxy-2-(4-hydroxy-3-hydroxymethyl-phenyl)-ethylamino]-hexyloxy}-butyl)-benzylsulphonamide, 3-(3-{7-[2-hydroxy-2-(4-hydroxy-3-hydroxymethyl-phenyl)-ethylamino]-heptyloxy}-propyl)-benzylsulphonamide, 4-(2-{6-[4-(3-cyclopentanesulphonyl-phenyl)-butoxy]-hexylamino}-1-hydroxy-ethyl)-2-hydroxymethyl-phenol, N-adamantan-2-yl-2-(3-{2-[2-hydroxy-2-(4-hydroxy-3-hydroxymethyl-phenyl)-ethylamino]-propyl}-phenyl)-acetamide, optionally in the form of their racemates, enantiomers, diastereomers and optionally in the form of their pharmacologically acceptable acid addition salts, solvates or hydrates. The preferred acid addition salts of the betamimetics according to the invention are those selected from among the hydrochloride, hydrobromide, hydriodide, hydrosulphate, hydrophosphate, hydromethanesulphonate, hydronitrate, hydromaleate, hydroacetate, hydro-citrate, hydrofumarate, hydrotartrate, hydrooxalate, hydrosuccinate, hydrobenzoate and hydro-p-toluenesulphonate.

The anticholinergics used here are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine and aclidinium, preferably as the bromide salt.

Other anticholinergics which are preferably used are selected from among tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate-methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide. The above-mentioned methobromides may also be used as salts within the scope of the present invention, by using, instead of the methobromide, the metho-X salts, wherein X is selected from among the fluoride, chloride, iodide, sulphate, phosphate, methanesulphonate, nitrate, maleate, acetate, citrate, fumarate, tartrate, oxalate, succinate, benzoate and p-toluenesulphonate.

The corticosteroids used here are preferably compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26, (S)-fluoromethyl 6,9-difluoro-17-[(2-furanylcarbonyl)oxy]-1-hydroxy-16-methyl-3-oxo-androsta-1,4-diene-17-carbothionate, (S)-(2-oxo-tetrahydro-furan-3 S-yl) 6,9-difluoro-11-hydroxy-16-methyl-3-oxo-17-propionyloxy-androsta-1,4-diene-17-carbothionate and cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate, optionally in the form of the racemates, enantiomers or diastereomers thereof and optionally in the form of the salts and derivatives thereof, the solvates and/oder hydrates thereof. Any reference to steroids includes a reference to any salts or derivatives, hydrates or solvates thereof that may exist. Examples of possible salts and derivatives of steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

The PDE4 inhibitors used here are preferably compounds selected from among enprofyllin, theophyllin, roflumilast, ariflo (cilomilast), oglemilast, tofimilast, pumafentrin, lirimilast, arofyllin, atizoram, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4 antagonists used here are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acide, 1-(((1(R)-3 (3-(2-(2,3-dichlorthieno[3,2-b]pyridin-5-yl)-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl] acetic acide, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

By salts or derivatives which the LTD4 antagonists may possibly be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

The EGFR-inhibitors used here are preferably compounds selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2- buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluorophenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluorophenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluorophenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluorophenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethinyl-phenyl)amino]-6,7-to-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluorobenzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-mor-pholin-4-yl)-1-oxo-2-buten-1-yl]amino}-quinazoline, 4-[(3-chloro-4-fluorophenyl)amino]-6-[2-(2,2-dimethyl-6-oxo-morpholin-4-yl)-ethoxy]-7-methoxy-quinazoline, 4-[(3-chloro-4-fluorophenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluorophenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluorophenyl)amino]-6-{2-[4-(2-oxo-morpholin-4-yl)-piperidin-1-yl]ethoxy}-7-methoxy-quinazoline, 4-[(3-chloro-4-fluorophenyl)amino]-6-[1-(tert.-butyloxycarbonyl)-piperidin-4-yloxy]-7-methoxy-quinazoline, 4-[(3-chloro-4-fluorophenyl)amino]-6-(trans-4-amino-cyclohexan-1-yloxy)-7-methoxy-quinazoline, 4-[(3-chloro-4-fluorophenyl)amino]-6-(trans-4-methane-sulphonylamino-cyclohexan-1-yloxy)-7-methoxy-quinazoline, 4-[(3-chloro-4-fluorophenyl)amino]-6-(tetrahydropyran-3-yloxy)-7-methoxy-quinazoline, 4-[(3-chloro-4-fluorophenyl)amino]-6-(1-methyl-piperidin-4-yloxy)-7-methoxy-quinazoline, 4-[(3-chloro-4-fluorophenyl)amino]-6-{1-[(morpholin-4-yl)carbonyl]-piperidin-4-yloxy}-7-methoxy-quinazoline, 4-[(3-chloro-4-fluorophenyl)amino]-6-{1-[(methoxymethyl)carbonyl]-piperidin-4-yloxy}-7-methoxy-quinazoline, 4-[(3-chloro-4-fluorophenyl)amino]-6-(piperidin-3-yloxy)-7-methoxy-quinazoline, 4-[(3-chloro-4-fluorophenyl)amino]-6-[1-(2-acetylamino-ethyl)-piperidin-4-yloxy]-7-methoxy-quinazoline, 4-[(3-chloro-4-fluorophenyl)amino]-6-(tetrahydropyran-4-yloxy)-7-ethoxy-quinazoline, 4-[(3-chloro-4-fluorophenyl)amino]-6-((S)-tetrahydrofuran-3-yloxy)-7-hydroxy-quinazoline, 4-[(3-chloro-4-fluorophenyl)amino]-6-(tetrahydropyran-4-yloxy)-7-(2-methoxy-ethoxy)-quinazoline, 4-[(3-chloro-4-fluorophenyl)amino]-6-{trans-4-[(dimethylamino)sulphonylamino]-cyclohexan-1-yloxy}-7-methoxy-quinazoline, 4-[(3-chloro-4-fluorophenyl)amino]-6-{trans-4-[(morpholin-4-yl)carbonylamino]-cyclohexan-1-yloxy}-7-methoxy-quinazoline, 4-[(3-chloro-4-fluorophenyl)amino]-6-{trans-4-[(morpholin-4-yl)sulphonylamino]-cyclohexan-1-yloxy}-7-methoxy-quinazoline, 4-[(3-chloro-4-fluorophenyl)amino]-6-(tetrahydropyran-4-yloxy)-7-(2-acetylamino-ethoxy)-quinazoline, 4-[(3-chloro-4-fluorophenyl)amino]-6-(tetrahydropyran-4-yloxy)-7-(2-methanesulphonylamino-ethoxy)-quinazoline, 4-[(3-chloro-4-fluorophenyl)amino]-6-{1-[(piperidin-1-yl)carbonyl]-piperidin-4-yloxy}-7-methoxy-quinazoline, 4-[(3-chloro-4-fluorophenyl)amino]-6-(1-aminocarbonylmethyl-piperidin-4-yloxy)-7-methoxy-quinazoline, 4-[(3-chloro-4-fluorophenyl)amino]-6-(cis-4-{N—[(tetrahydropyran-4-yl)carbonyl]-N-methyl-amino}-cyclohexan-1-yloxy)-7-methoxy-quinazoline, 4-[(3-chloro-4-fluorophenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluorophenyl) amino]-6-(cis-4-{N—[(morpholin-4-yl)sulphonyl]-N-methyl-amino}-cyclohexan-1-yloxy)-7-methoxy-quinazoline, 4-[(3-chloro-4-fluorophenyl)amino]-6-(trans-4-ethane-sulphonylamino-cyclohexan-1-yloxy)-7-methoxy-quinazoline, 4-[(3-chloro-4-fluorophenyl)amino]-6-(1-methane-sulphonyl-piperidin-4-yloxy)-7-ethoxy-quinazoline, 4-[(3-chloro-4-fluorophenyl)amino]-6-(1-methanesulphonyl-piperidin-4-yloxy)-7-(2-methoxy-ethoxy)-quinazoline, 4-[(3-chloro-4-fluorophenyl)amino]-6-[1-(2-methoxy-acetyl)-piperidin-4-yloxy]-7-(2-methoxy-ethoxy)-quinazoline, 4-[(3-chloro-4-fluorophenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluorophenyl)amino]-6-(cis-4-{N—[(piperidin-1-yl)carbonyl]-N-methyl-amino}-cyclohexan-1-yloxy)-7-methoxy-quinazoline, 4-[(3-chloro-4-fluorophenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluorophenyl)amino]-

6-{cis-4-[(morpholin-4-yl)carbonylamino]-cyclohexan-1-yloxy}-7-methoxy-quinazoline, 4-[(3-chloro-4-fluorophenyl)amino]-6-{1-[2-(2-oxopyrrolidin-1-yl)ethyl]-piperidin-4-yloxy}-7-methoxy-quinazoline, 4-[(3-chloro-4-fluorophenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluorophenyl)amino]-6-(1-methyl-piperidin-4-yloxy)-7(2-methoxy-ethoxy)-quinazoline, 4-[(3-chloro-4-fluorophenyl)amino]-6-(1-isopropyloxycarbonyl-piperidin-4-yloxy)-7-methoxy-quinazoline, 4-[(3-chloro-4-fluorophenyl)amino]-6-(cis-4-methylamino-cyclohexan-1-yloxy)-7-methoxy-quinazoline, 4-[(3-chloro-4-fluorophenyl)amino]-6-{cis-4-[N-(2-methoxy-acetyl)-N-methyl-amino]-cyclohexan-1-yloxy}-7-methoxy-quinazoline, 4-[(3-ethynyl-phenyl) amino]-6-(piperidin-4-yloxy)-7-methoxy-quinazoline, 4-[(3-ethynyl-phenyl) amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluorophenyl)amino]-6-{1-[(cis-2,6-dimethyl-morpholin-4-yl)carbonyl]-piperidin-4-yloxy}-7-methoxy-quinazoline, 4-[(3-chloro-4-fluorophenyl)amino]-6-{1-[(2-methyl-morpholin-4-yl)carbonyl]-piperidin-4-yloxy}-7-methoxy-quinazoline, 4-[(3-chloro-4-fluorophenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluorophenyl)amino]-6-{1-[(N-methyl-N-2-methoxyethyl-amino)carbonyl]-piperidin-4-yloxy}-7-methoxy-quinazoline, 4-[(3-chloro-4-fluorophenyl)amino]-6-(1-ethyl-piperidin-4-yloxy)-7-methoxy-quinazoline, 4-[(3-chloro-4-fluorophenyl)amino]-6-{1-[(2-methoxyethyl)carbonyl]-piperidin-4-yloxy}-7-methoxy-quinazoline, 4-[(3-chloro-4-fluorophenyl)amino]-6-{1-[(3-methoxypropyl-amino)-carbonyl]-piperidin-4-yloxy}-7-methoxy-quinazoline, 4-[(3-chloro-4-fluorophenyl)amino]-6-[cis-4-(N-methanesulphonyl-N-methyl-amino)-cyclohexan-1-yloxy]-7-methoxy-quinazoline, 4-[(3-chloro-4-fluorophenyl)amino]-6-[cis-4-(N-acetyl-N-methyl-amino)-cyclohexan-1-yloxy]-7-methoxy-quinazoline, 4-[(3-chloro-4-fluorophenyl)amino]-6-(trans-4-methylamino-cyclohexan-1-yloxy)-7-methoxy-quinazoline, 4-[(3-chloro-4-fluorophenyl) amino]-6-[trans-4-(N-methanesulphonyl-N-methyl-amino)-cyclohexan-1-yloxy]-7-methoxy-quinazoline, 4-[(3-chloro-4-fluorophenyl)amino]-6-(trans-4-dimethylamino-cyclohexan-1-yloxy)-7-methoxy-quinazoline, 4-[(3-chloro-4-fluorophenyl)amino]-6-(trans-4-{N—[(morpholin-4-yl)carbonyl]-N-methyl-amino}-cyclohexan-1-yloxy)-7-methoxy-quinazoline, 4-[(3-chloro-4-fluorophenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluorophenyl)amino]-6-(1-methanesulphonyl-piperidin-4-yloxy)-7-methoxy-chinazolin and 4-[(3-chloro-4-fluorophenyl)amino]-6-(1-cyano-piperidin-4-yloxy)-7-methoxy-quinazoline, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used here are preferably compounds selected from among bromocriptin, cabergolin, alpha-dihydroergocryptin, lisuride, pergolide, pramipexol, roxindol, ropinirol, talipexol, tergurid and viozan, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The H1-antihistamines used here are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorphenoxamine, dimenhydrinate, diphenhydramine, promethazine, ebastine, desloratidine and meclozine, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydro-citrate, hydrofumarate, hydrotartrate, hydroxalate, hydrosuccinate, hydrobenzoate and hydro-p-toluenesulphonate.

The invention claimed is:

1. A process for monitoring the filling of a capsule with a medicament comprising the steps of:
    filling at least part of the capsule with a given fill mass of a given closed contour from the medicament;
    recording an image of at least the fill mass of the medicament contained in the capsule and transmitting the image to a computer in computer-readable format; and
    evaluating, by computer, the filling using the image by determining the contour of the fill mass contained in the capsule,
    wherein determining the contour of the fill mass contained in the capsule involves accessing the recorded image, using a suitable algorithm to approximate a contour line of the fill mass in the recorded image by convex matching to give an approximated contour line and comparing the length of the approximated contour line with the length of a predetermined contour line; and
    analyzing whether a correct fill quantity is in the capsule.

2. The process to claim 1, wherein in the recording step, the image recording is carried out using visible light.

3. The process according to claim 1, wherein in the recording step, the image recording is carried out by means of a recording that penetrates the capsule part.

4. The process according to claim 1, wherein in the recording step, interior part of the capsule part is captured in its entirety.

5. The process according to claim 1, wherein in the recording step, the image recording is carried out from above the capsule into an interior part of the capsule.

6. The process according to claim 1, wherein the filled part of the capsule is moved at least during the recording step.

7. The process according to claim 1, wherein in the evaluation step, the contour recorded is examined for concave areas.

8. The process according to claim 1, wherein the given contour is predetermined by a cylindrical fill mass.

9. The process according to claim 1, wherein in the evaluation step, contrast is increased and/or grey or color gradations of the image are reduced.

10. The process according to claim 1, wherein in the evaluation step, the image is converted into a binary image.

11. The process according to claim 1, wherein in the evaluation step, the image is subjected to morphological edge recognition in order to establish a contour line.

12. A process for the continuous mechanical filling of a capsule with a medicament comprising the steps of:
   filling at least part of the capsule with a specified fill mass of a given closed contour from the medicament;
   monitoring the filling by recording an image of at least the fill mass of the medicament contained in the capsule and transmitting the image to a corm cuter in computer-readable format;
   evaluating, by computer, the filling using the image by determining the contour of the fill mass contained in the capsule;
   wherein determining the contour of the mass contained in the capsule involves accessing the recorded image, using a suitable algorithm to approximate a contour line of the fill mass in the recorded image by convex matching to give an approximated contour line and comparing the length of the approximated contour line with the length of a predetermined contour line;
   analyzing whether a correct fill quantity is in the capsule; and
   using the results of the monitoring to reject the capsule if necessary.

13. The according to claim 12, wherein the filling comprises knocking the fill mass onto at least a part of the capsule.

14. The process according to claim 12, wherein the medicament that forms the fill mass is in powder form.

15. The process according to claim 12, wherein the filling is carried out using a pipette technique.

16. An apparatus for monitoring a filling of a capsule with a medicament, comprising:
   a digital image recording unit operating to record an image of at least a fill mass of a given closed contour of the medicament contained in the capsule and transmitting the image to a computer in computer-readable format;
   a digital image analysis unit operating to: (i) evaluate, by computer, the filling using the image by determining the contour of the fill mass contained in the capsule, wherein determining the contour of the fill mass contained in the capsule involves accessing the recorded image, using a suitable algorithm to approximate a contour line of the fill mass in the recorded image by convex matching to give an approximated contour line and comparing the length of the approximated contour line with the length of a predetermined contour line, and (ii) analyzing whether a correct fill quantity is in the capsule.

17. The apparatus according to the claim 16, wherein the digital image recording unit comprises at least one CCD (4) or CMOS image converter.

18. The apparatus according to claim 16, wherein the digital image recording unit comprises at least one LED (6) or a laser.

19. The process according to claim 1, wherein the medicament is a powdered medicament.

20. The process according to claim 1, wherein the recorded image is a digital image.

* * * * *